United States Patent [19]

Taller et al.

[11] Patent Number: 4,737,219
[45] Date of Patent: Apr. 12, 1988

[54] METHOD FOR BONDING POLYURETHANE BALLOONS TO MULTILUMEN CATHETERS

[75] Inventors: Robert A. Taller, Centerville; Charles Daugherty, Xenia, both of Ohio

[73] Assignee: Becton, Dickinson and Company, Franklin Lakes, N.J.

[21] Appl. No.: 932,856

[22] Filed: Nov. 20, 1986

Related U.S. Application Data

[62] Division of Ser. No. 700,779, Feb. 12, 1985, Pat. No. 4,661,095.

[51] Int. Cl.⁴ .................... B28B 11/06; B28B 1/38
[52] U.S. Cl. ........................ 156/215; 156/242; 156/245; 264/131; 264/250; 264/254; 264/255; 264/304; 264/305
[58] Field of Search ............... 604/103; 264/301, 302, 264/303, 304, 305, 306, 317, 230, 250, 251, 254, 255, 258, 131, 137, 138, 139, DIG. 57; 156/160, 165, 182, 184, 185, 187, 242, 245, 247, , 248, 250, 428, 429, 215, 62.2

[56] References Cited

U.S. PATENT DOCUMENTS

| | | | |
|---|---|---|---|
| 2,230,138 | 1/1941 | Ewart | 264/306 |
| 2,308,484 | 1/1943 | Auzin et al. | 264/305 |
| 2,318,682 | 5/1943 | Fawick | 264/306 |
| 2,481,488 | 9/1949 | Auzin | 264/305 |
| 3,539,674 | 11/1970 | Dereniuk | 264/306 |
| 4,003,382 | 1/1977 | Dyke | 604/103 |

Primary Examiner—James Lowe
Assistant Examiner—J. F. Durkin, II
Attorney, Agent, or Firm—Robert P. Grindle

[57] ABSTRACT

A process for making a balloon for use on a multilumen catheter using as a form for the balloon a mandrel having at least one groove and at least one score line. The mandrel is rotated while metering into the groove a thermoplastic adhesive. The balloon stock is formed by coating the mandrel with a solid thermosetting polyurethane prepolymer. After cooling of the mandrel a film of thermoplastic adhesive is wrapped over the balloon at about the score line. Once the assembly is cured the balloon stock is removed to result in a balloon having an adhesive film on the internal wall at one end and an adhesive film on the external wall at the other end.

8 Claims, 3 Drawing Sheets

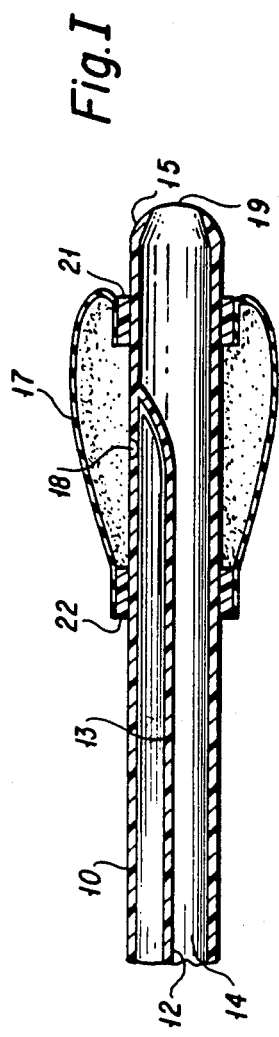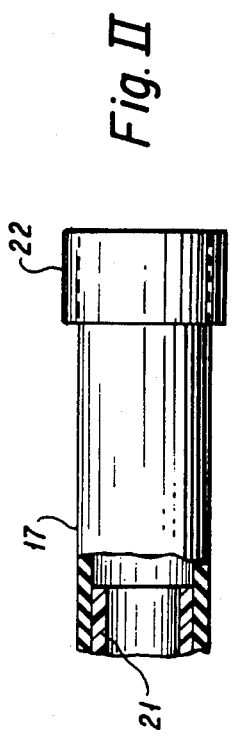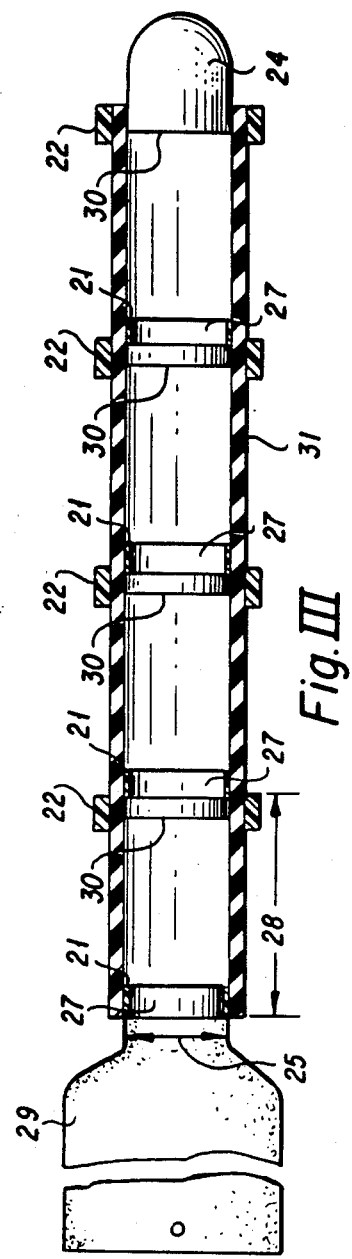

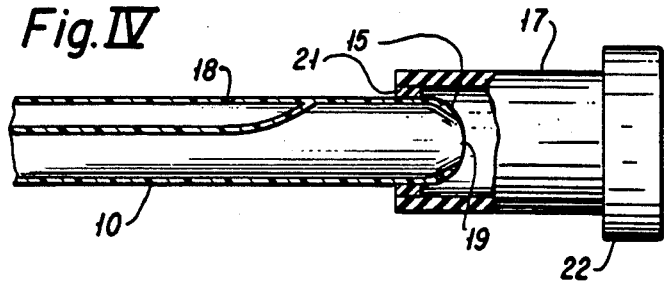
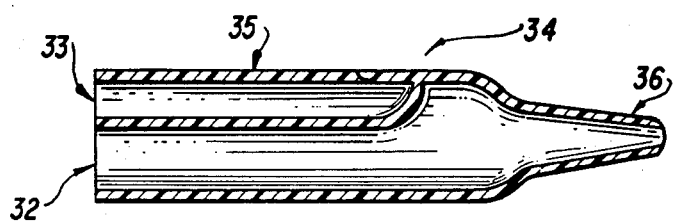
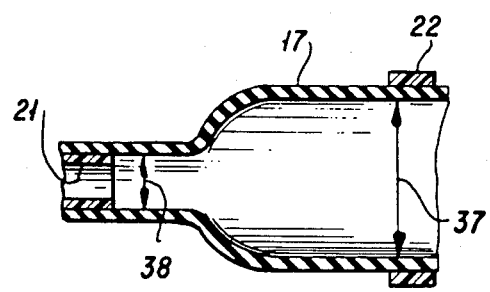

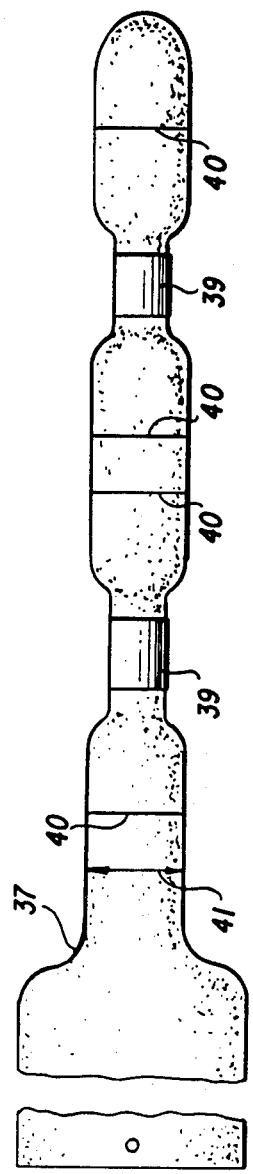

METHOD FOR BONDING POLYURETHANE BALLOONS TO MULTILUMEN CATHETERS

This is a division of application Ser. No. 700,779, filed Feb. 12, 1985 now U.S. Pat. No. 4,661,095.

FIELD OF THE INVENTION

This invention relates to balloon catheters. In particular, it relates to a method for securing balloons made of thermosetting polyurethane elastomer to plastic catheters.

BACKGROUND OF THE INVENTION

Catheters have been in use for many years and traditionally comprise a flexible and resilient body portion having, generally, an inflation lumen and one or more other lumens for withdrawing blood specimens, monitoring blood pressure and temperature, or introduction of drugs extending through the body portion. An opening is provided in the catheter wall extending into and communicating with the inflation lumen and an inflatable balloon is secured to the catheter over the opening thereby permitting the inflation of the balloon by introducing a fluid pressure through the inflation lumen. The distal end of the catheter adapted for insertion into the patient is normally rounded. Openings are provided in the catheter wall communicating with the lumens used for withdrawing blood specimens, monitoring blood pressure and temperature, or introduction of drugs, the openings generally being located intermediate the balloon and the catheter distal end.

At the opposite, proximal, end of the catheter, funnel portions are provided communicating with the lumens. In multilumen catheters the tubular body is normally bifurcated adjacent to the proximal ends of the inflation lumen.

U.S. Pat. No. 4,003,382 which discloses a method for preparing thermosetting polyurethane balloons that are added to a catheter body made of thermoplastic polyurethane. The balloon is procuced by first applying a heat activatable polyurethane adhesive to a mandrel either in strips or from solution. A thermosetting polyurethane balloon is then formed on the mandrel using a mold which is filled with the thermosetting polyurethane and heated to form and cure the polymer. The resulting product is a polyurethane tubular sleeve having polyurethane adhesive bands on the inside of the tube at each end. This balloon is then slipped over a catheter covering the inflating lumen, and sealed in place by heat activating the polyurethane adhesive bands. This construction results in a catheter in which the distal end is a sharp protrusion extending beyond the balloon thereby presenting a hazard to a patient in whom the catheter has been inserted.

U.S. Pat. No. 3,746,003 and a related U.S. Pat. No. 3,634,924 disclose a balloon construction which to some extent alleviates the problem of a hazardous lead point on the catheter by utilizing a balloon construction wherein the tube from the the balloon is attached to the distal end of the catheter and everted. The result is a balloon configuration which when inflated, extends forward of the area of attachment and the distal end of the catheter. In the '003 and '924 patents, however, the balloon is held in place by winding of thread over a metal ferrules. The function of the ferrules is to prevent the windings from collapsing the catheter tube. Inadvertent dislodgement of windings result in a hazard to the patient.

U.S. Pat. No. 4,403,084 discloses a crystalline grindable polyurethane prepolymer. The polymer can be formed into objects by causing the prepolymer to form a film on a mandrel heated above the melting point of the prepolymer. The film is then heated to cure it. The use of the prepolymer to prepare surgical gloves in this manner is disclosed.

SUMMARY OF THE INVENTION

It has surprisingly been found that a balloon can be attached to a catheter in a reverse lap configuration by utilizing thermoplastic adhesive. An adhesive band internal to a tube used to form the balloon is used to adhere the tube to the distal end of the catheter. An adhesive band external to the tube at its other end is used to secure the tube to the catheter by everting the tube and adhering it to the catheter body at a position away from the distal end and enclosing an opening in the catheter wall communicating with an inflation lumen in the catheter body. In its preferred embodiment the balloon is formed of thermosetting polyurethane elastomer and the adhesive bands are formed of thermoplastic polyurethane.

In preparing the balloon a thermoplastic polyurethane adhesive materials is applied to a mandrel which is then coated with a film of polyurethane prepolymer by heating the mandrel and dipping it into prepolymer powder. A thermoplastic polyurethane adhesive band is then applied to the other end of the balloon and the balloon is cured.

The method of this invention permits the balloon to be placed at the distal end of the catheter in a reverse lap configuration so that when the balloon is inflated it extends forward over the distal end of the catheter. The use of thermosetting polyurethane polymer for the balloon adds an additional safety feature in that should the polyurethane balloon rupture it merely splits rather than fragmenting as do latex balloons.

BRIEF DESCRIPTION OF DRAWINGS

FIG. I Catheter with Balloon in Reverse Lap Configuration
FIG. II Balloon with Adhesive Bands
FIG. III Mandrel with Balloon Stock and Adhesive Bands in Place
FIG. IV Catheter and Balloon
FIG. V Two Step Catheter
FIG. VI Two Step Mandrel
FIG. VII Two Step Balloon

DETAILED DESCRIPTION

The catheter bodies suitable for use in the instant invention can be fabricated in accordance with conventional procedures known to the art. The preferred material for the catheter body is thermoplastic polyurethane. Referring now to FIG. I, in one typical manufacturing procedure the catheter body, 10, is formed by extrusion into a cylindrical tube, 10, having an elongated internal portion, 12, which divides the interior of the catheter body, 10, into an inflation lumen, 13, and at least one fluid injection lumen, 14. The extrusion process produces an open ended cylindrical tube, the distal end, 15, of which is rounded by conventional heat molding techniques. Before attaching the inflation balloon, 17, an inflation port, 18, is punched through the wall of the catheter body, 10, near the distal end, 15, of the catheter and communicating with the inflating lumen, 13. Similarly, an open port, 19, communicates through the wall of the catheter body at the distal end, 15, communicating with the fluid delivery lumen, 14. A coating or release agent can be applied about the catheter shaft, 10, in the area of the inflation port, 18, in order to ensure that the balloon, 17, does not adhere to the catheter body, 10.

The balloon of this invention is manufactured out of a thermosetting polyurethane polymer. Referring now to FIG. II, the balloon body, 17, can be in tubular form or tapered and has bands of adhesive, 21 and 22, one on the inside surface of the tube and the other on the outside surface of the tube and at the opposite end from the other band. As shown in FIG. IV, the balloon, 17, is slipped over the distal end of the catheter and secured by heat activating the band, 21. The balloon is then everted and drawn back over inflation port, 18, and secured by heat activating the bond, 22, to form a reverse lap configuration balloon.

In the practice of this invention, the balloon is prepared on a mandrel. Referring now to FIG. III, the length of the mandrel, 24, is not critical, but preferably varies from about 7.5 cm to about 15 cm. The mandrel diameter, 25, will depend on the French size of the catheter tip for which the balloon is being prepared and can vary from about 1 mm to about 2.5 mm. Circular grooves, 27, about 0.0125 mm to about 0.05 mm deep are cut into the mandrel. The space, 28, between grooves, from the beginning of one groove to the beginning of the subsequent groove is equal to about the length of the balloon to be prepared. The mandrel, 24, is attached to a supporting base rod, 29.

In order to prevent the balloon stock and adhesive bands, 21, from adhering to the mandrel, the mandrel is coated with a release agent, preferably a polytetrafluoroethylene release agent (PTFE). A solution of thermoplastic polyurethane adhesive is prepared from which the adhesive bond is made. The mandrel, 24, is secured in a lathe chuck by means of the base, 29, and slowly rotated while the adhesive solution is metered into the grooves, 27, to form a 2 mm wide adhesive band. The grooves, 27, prevent the adhesive from spreading while it is drying and thus provide an adhesive band of uniform thickness as well as a defined band front. The mandrel is rotated until the adhesive dries. While evaporation of solvent from the adhesive solution is preferably accomplished at ambient conditions, elevated temperatures can be utilized.

The mandrel coated with the adhesive bands is heated to between 125° C. to about 175° C. and dipped into a fluidized bed of polyurethane prepolymer powder coating. Where the mandrel temperature is about 10° C. above the melting point of the prepolymer, particles will adhere to the mandrel which can be fused into a film. Preferably, the mandrel temperature is about 50° C. higher than the melting point of the prepolymer and a film of prepolymer forms on the mandrel directly. The wall thickness of the prepolymer which forms the balloon stock, 31, can be controlled by varying the mandrel temperature and dip rate. The coated mandrel is cooled to room temperature and an adhesive film band, 22, is wrapped around the polyurethane balloon stock, 31, at each of the score marks, 30. If desired the length of the balloon can be varied by placing the adhesive band, 22, at the score line, 30, over the score line, 30, or midpoint of the score line, 30.

The coated mandrel, 24, with balloon stock, 31, and adhesive bands, 21 and 22, is placed in a convection oven and rotated horizontally while heating at a temperature of 150° C. for about 30 to 50 minutes to cure the prepolymer. The mandrel, 24, is cooled to room temperature and the balloon stock, 31, is stripped off the mandrel using an air stripping device which lifts the balloon off the mandrel. Any suitable means may be used for stripping the balloon off the mandrel. Air is preferred since it results in a minimum of damage to the balloon. Individual balloons, 17, are cut from the balloon stock, 31, and inspected to ensure that they are free of defects.

As shown in FIG. IV a balloon, 17, is slipped over the distal end of the catheter, 10, sufficiently past the distal end, 15, so that the adhesive bond, 21, does not cover the open port, 19. The adhesive strip, 21, is heat sealed to the catheter body, 10, by heating the balloon catheter assembly in yokes which are the width of the band, 21, and have two sections each having a semi-circular opening which is slightly smaller than the diameter of balloon, 17, plus adhesive band, 22. In a preferred embodiment the yokes are made of aluminum and electrically heated. These pneumatic pressure activated yokes close around the balloon-adhesive band area thereby bonding the balloon, 17, to the catheter, 10. A typical bonding cycle is 20 to 120 seconds at 130° C. to 150° C. The cycle will depend on the catheter hardness, and bonding temperatures can vary from about 110° C. to about 150° C. depending on the adhesive formulation. Determination of the particular bonding cycle to be used is well within the capability of those skilled in the art. Generally the supplier of the adhesive will recommend cycle temperatures, but no extensive experimentation is required to optimize bonding cycles and temperature.

After the catheter with the balloon bonded to its distal end has cooled, the balloon is everted and drawn back over it and beyond the inflation port, 18, and bonded to the catheter at a point away from the distal end and toward the proximal end. The same procedure and cycle is used to bond the adhesive bond, 22, to the catheter body. The result is a catheter with balloon attached in the reverse flap configuration as shown in FIG. I.

Two step catheters similar to those shown in FIG. V have at least one fluid injection lumen, 32, and an inflation lumen, 33, communicating with an inflation port, 34, in the wall of the catheter tube, 35, as do the previously described catheters. However, the distal end, 36, of the catheter is smaller in diameter than the body, 35. These catheters with balloon attached can be inserted through a smaller introducer catheter than a conventional catheter of the same French size.

In order to prepare balloons for the two step catheter a mandrel having steps is required. As shown in FIG. VI, the mandrel, 37, has a major diameter, 41, which corresponds to the catheter body and a necked down portion, 39, which corresponds in diameter to the necked down distal end of the catheter. The necked down section, 39, of the mandrel, 37, is grooved to accept the polyurethane adhesive solution. The width of the groove is two adhesive band widths, e.g., 4 mm. Adhesive solution is added in the manner previously described. After drying the mandrel, 37, with adhesive bands is immersed in powdered polyurethane to form the balloon stock. Additional adhesive bands are wrapped around the balloon stock at score lines, 40, and the balloon stock cured in the manner described. After cooling the mandrel the balloon stock is removed and cut into four individual balloons suitable for use with two step catheters.

A balloon for a two step catheter is shown in FIG. VII. The balloon, 17, has a major diameter, 37, which corresponds to the distal end, 36, of the two step catheter and a minor diameter, 38, which corresponds to the body, 35, of the catheter. The internal adhesive bond, 21, is the minor diameter (distal) end of the balloon.

The advantage of this invention may be more readily appreciated by reference to the following example:

EXAMPLE I-III

A thermoplastic polyurethane adhesive solution was prepared having the following formulation:

| Component | Grams |
|---|---|
| 2000 M.W. Polycaprolactone diol | 74.8 |
| 1,4 Butanediol | 3.8 |
| Methylene bis (4-cyclohexyl-isocyanate) | 21.4 |
| Catalyst (Stannous octoate) | 0.1 |

The solution was prepared at 4 wt. % polymer components in tetrahydrofuran.

The mandrel shown in FIG. I was set up in a chuck and rotated 200 to 300 rpm while adhesive solution was metered into the grooves. The process was continued until the dried adhesive filled the grooves. The mandrel was then heated to 175° C. and immersed in polyurethane prepolymers, as described in Table I, for 3 seconds. The balloon stock film which deposited on the hot mandrel had a wall thickness of about 0.203 mm. The balloon stock was then cooled to room temperature.

A ten percent (10%) solution of polyurethane adhesive (see above formulation) was prepared and air dried on a vapor honed glass plate to form a 0.0254 mm film of adhesive polyurethane. The adhesive was cut into strip 2 mm wide and 9 mm long and wrapped around the balloon stock at the score line of the mandrel.

The mandrel was then mounted horizontally on a rotating fixture and placed in an air convection oven for 30 minutes at 150° C. to cure the polyurethane prepolymer. The mandrel was cooled to room temperature and the balloon stock air stripped from the mandrel. The stock was cut into four individual balloons. The physical properties of the balloons are shown in Table II. A balloon which had an I.D. of about 1.65 to about 1.93 mm was slipped over the distal end of 7 a French type catheter so that the internal adhesive band was at the distal end. The balloon was bonded to the catheter by installing the balloon catheter assembly in heated yokes, the yokes closing over the band portion of the balloon thereby fusing the adhesive band onto the catheter. A temperature of 130° to 150° C. was used to make the bond. Pressure was applied for 10 to 60 seconds.

After cooling the balloon and catheter, the balloon was everted and drawn back over the catheter balloon inflation part and bonded to the catheter. This configuration as depicted in FIG. I is referred to as a reversed lap configuration.

TABLE I

POLYURETHANE BALLOON FORMULATIONS

| REACTANTS (weight, grams) | EXAMPLE 1 | EXAMPLE 2 | EXAMPLE 3 |
|---|---|---|---|
| 540 M.W. Polycaprolactone[a] Triol (Tone TM 305 Polyol) | 16.9 | 15.0 | 17.7 |
| 2000 M.W. Poly (ethylene adipate) diol | 107.5 | 107.4 | 105.0 |
| 3000 M.W. Poly(ethylene-butylene adipate) diol | 180.5 | 181.0 | 177.0 |
| Dow Corning Q4-3667 | 20.1 | 20.4 | 21.1 |
| 1,4 butanediol | 6.5 | 7.3 | 7.5 |
| 4,4' Diphenylmethane Diisocyanate | 61.6 | 62.5 | 64.5 |
| Acetone Oxime | 6.9 | 6.4 | 7.2 |
| Dibutyltin Dilaurate | 0.8 | 0.8 | 0.8 |
| Hard Segment, % | 17.0 | 17.4 | 18.0 |
| Mc | 8700 | 9300 | 8300 |
| Long Chain diol, % | 77.0 | 77.2 | 75.8 |
| Crosslinking Agent, % | 4.2 | 3.8 | 4.4 |
| Diisocyanate Content, % | 15.4 | 15.6 | 16.1 |

DOW CORNING Q4-3667 - 2400 M.W. - polydimethylsiloxanepolyethylene copolymer diol.
Mc - Degree of cross-linking, defined as the molecular weight between chemical cross-links. (See U.S. Pat. No. 4,434,126 McGary Jr. et al. (Column 4, Line 5).

TABLE II

PHYSICAL PROPERTIES OF POLYURETHANE AND NATURAL RUBBER LATEX FILMS AND BALLOONS

| | Example | | | Natural Rubber |
|---|---|---|---|---|
| Tensile Moduli, psi | 1 | 2 | 3 | |
| 10% | 30 | 35 | 40 | 20 |
| 100% | 130 | 140 | 160 | 100 |
| 300% | 210 | 240 | 290 | 210 |
| 500% | 350 | 450 | 580 | 490 |
| Ultimate Tensile Strength, psi | 4000 | 4300 | 4200 | 3500 |
| Tensile Elongation, % | 770 | 740 | 670 | 750 |
| Tensile Set, % | 10 | 4 | 2 | 5 |
| Balloon Initial Inflation Pressure, psi | 12[a] | 13[a] | 14[a] | 8-10[b] |
| Balloon Burst Pressure, psi | >20[a] | >20[a] | >20[a] | 13[b] |

[a]Values determined at 37° C. for 6.0 mil balloon wall thickness
[b]Values for 8.0 mil balloon wall thickness This invention is not intended to be limited by the composition of either the thermoplastic polyurethane adhesive or the termosetting polyurethane prepolymer. Any suitable composition known in the art as useful in balloons may be used for the balloon stock. Similarly any thermoplastic polyurethane can be used as the adhesive provided that its melting point is below that of the catheter body.

In its preferred embodiment the polyurethane prepolymer is used as a powder having a particle size of about 20 to 75 microns. An amorphous fused silica (ca 4 microns) can be mixed with the prepolymer powder to improve powder bed fluidization and film forming characteristics of the prepolymer film.

The width of the adhesive bands applied to the balloon, either directly or from the mandrel, is not critical. However, it has been found that the width of the adhesive band is preferably about 1 mm to about 2.5 mm, more preterably 2 mm. The thickness of the adhesive layer is preferably about 0.0254 mm. Thicker layers may be utilized, however, no significant advantage is seen in their utilization.

The balloon wall thickness should be at least 0.102 mm to about 0.254 mm, more preferably about 0.178 mm.

The term "two step" configuration as used in the specification and claims with respect to the balloons of this invention means balloons or the configuration shown in FIG. VII. As is evident from the drawings the balloons have elongated cylindrical shapes of annular cross section. The term "wall," as used with reference to the balloon, in the specification and claims means the thickness of the annular cross section.

What is claimed is:

1. A process for making a balloon for use on a multilumen catheter, said balloon having a cylindrical configuration and an annular cross section and at least one inside diameter, said annular cross section being bounded by an internal wall and an external wall, which comprises:
   a. using as a form for the balloon a mandrel having a diameter substantially the same as that of the multilumen catheter with which the balloon is to be used, and having at least one groove of a finite width and at least one score line, said groove and score line being spacially oriented in relation to one another so that the distance between the score line and the groove including the width of the groove is about the length of the balloon said mandrel having means for mounting the mandrel in a chuck;
   b. mounting the mandrel in a chuck and rotating said mandrel while metering into the groove a solution of a thermoplastic adhesive, for a time sufficient to fill the groove with the adhesive, and drying the adhesive by permitting the solvent to evaporate;
   c. forming a balloon stock by coating the mandrel with a solid thermosetting polyurethane prepolymer having a melting point, by heating the mandrel to a temperature which is at least 10° C. above the melting point of the prepolymer and dipping the heated mandrel into a bed of powdered prepolymer for a time sufficient to coat the mandrel with prepolymer;
   d. cooling the mandrel to about room temperature;
   e. wrapping a film of thermoplastic adhesive over the balloon stock at about the score line;
   f. curing the balloon stock by heating at a temperature and time sufficient to effect a cure of the thermosetting polyurethane prepolymer;
   g. cooling the mandrel and balloon stock; and
   h. removing the balloon stock from the mandrel;
thereby forming at least one balloon having a thermoplastic polyurethane adhesive film on the internal wall of the balloon at a distal end and thermoplastic adhesive film around the internal balloon wall at a proximal end of the balloon.

2. The process according to claim 1 wherein the mandrel comprises a multiplicity of grooves and score lines.

3. The process according to claim 1 wherein the thermosetting polyurethane coating is cured in an air convection oven while rotating the mandrel.

4. The process according to claim 1 wherein the mandrel is heated to a temperature which is at least 50° C. above the melting point of the polyurethane prepolymer prior to dipping into the prepolymer powder.

5. A process for making a balloon for use on a multilumen two step catheter said balloon having a two step cylindrical configuration and an annular cross section with a distal end and a proximal end the distal end having a minor inside diameter which is less than a major inside diameter of the proximal end, said annular cross section being bounded by an internal wall and an external wall which comprises:
   a. using as a form for the balloon a mandrel having a two step configuration with a major diameter and at least one minor diameter said diameters being substantially the same as the corresponding diameters of the catheter with which the balloon is to be used, and having at least one groove of a finite width on the minor diameter and at least one score line on the major diameter, said groove and score line being spacially oriented in relation to one another so that the distance between the score line and a center point of the width of the groove is about the length of the balloon, said mandrel having means for mounting the mandrel in a chuck;
   b. mounting the mandrel in a chuck and rotating said mandrel while metering into the groove a solution of a thermoplastic adhesive, for a time sufficient to fill the groove with the adhesive, and drying the adhesive by permitting the solvent to evaporate;
   c. forming a balloon stock by coating the mandrel with a solid thermosetting polyurethane prepolymer having a melting point by heating the mandrel to a temperature which is at least 10° C. above the melting point of the prepolymer and dipping the heated mandrel into a bed of powdered prepolymer for a time sufficient to coat the mandrel with prepolymer;
   d. cooling the mandrel to about room temperature;
   e. wrapping a film of thermoplastic adhesive over the balloon stock at about the score line;
   f. curing the balloon stock by heating at a temperature and time sufficient to effect a cure of the thermosetting polyurethane polymer;
   g. cooling the mandrel and balloon stock; and
   h. removing the balloon stock from the mandrel.

6. The process according to claim 5 wherein the mandrel comprises a multiplicity of grooves and score lines.

7. The process according to claim 5 wherein the thermosetting polyurethane coating is cured in an air convection oven while rotating the mandrel.

8. The process according to claim 5 wherein the mandrel is heated to a temperature which is at least 50° C. above the melting point of the polyurethane prepolymer prior to dipping into the polyurethane prepolymer powder.

* * * * *